US011622886B2

(12) United States Patent
Govari et al.

(10) Patent No.: US 11,622,886 B2
(45) Date of Patent: Apr. 11, 2023

(54) THERMOCOUPLE COUPLED WITH A PIEZOELECTRIC CRYSTAL FOR FEEDBACK ON VIBRATION FREQUENCY

(71) Applicant: JOHNSON & JOHNSON SURGICAL VISION, INC., Santa Ana, CA (US)

(72) Inventors: Assaf Govari, Haifa (IL); Vadim Gliner, Haifa (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 312 days.

(21) Appl. No.: 16/876,201

(22) Filed: May 18, 2020

(65) Prior Publication Data

US 2021/0353461 A1    Nov. 18, 2021

(51) Int. Cl.
*A61F 9/007* (2006.01)
*A61B 18/14* (2006.01)
*A61B 17/32* (2006.01)

(52) U.S. Cl.
CPC ...... *A61F 9/00745* (2013.01); *A61B 18/1477* (2013.01); *A61F 9/00781* (2013.01); *A61B 2017/320069* (2017.08); *A61B 2018/1425* (2013.01)

(58) Field of Classification Search
CPC ............ A61F 9/00745; A61F 9/00781; A61B 18/1477; A61B 2017/320069; A61B 2018/1425; A61B 2018/00821
See application file for complete search history.

(56) References Cited

U.S. PATENT DOCUMENTS

| | | | |
|---|---|---|---|
| 4,954,960 A | * | 9/1990 | Lo .................. B06B 1/0253 331/181 |
| 5,158,087 A | * | 10/1992 | Gatzke .................. A61B 5/01 600/459 |
| 6,193,683 B1 | | 2/2001 | Ludin et al. |
| 6,979,328 B2 | | 12/2005 | Baerveldt et al. |
| 7,135,029 B2 | | 11/2006 | Makin et al. |
| 9,867,736 B2 | | 1/2018 | Morlet |
| 2009/0124960 A1 | | 5/2009 | Mackool |

FOREIGN PATENT DOCUMENTS

| | | |
|---|---|---|
| CN | 1299657 C | 2/2007 |
| CN | 101528350 B | 11/2012 |
| EP | 0270819 A2 | 6/1988 |
| EP | 0942696 A1 | 9/1999 |

\* cited by examiner

*Primary Examiner* — Peter Luong
(74) *Attorney, Agent, or Firm* — Johnson & Johnson Surgical Vision, Inc.

(57) ABSTRACT

A phacoemulsification device includes a needle, one or more piezoelectric crystals, and one or more thermocouples. The needle is configured for insertion into a lens capsule of an eye. The one or more piezoelectric crystals are configured to vibrate the needle. The one or more thermocouples are thermally coupled directly to the respective piezoelectric crystals and are configured to measure respective temperatures of the one or more piezoelectric crystals as the crystals vibrate, and to output indications of the respectively measured temperatures.

6 Claims, 2 Drawing Sheets

THERMOCOUPLE COUPLED WITH A PIEZOELECTRIC CRYSTAL FOR FEEDBACK ON VIBRATION FREQUENCY

FIELD OF THE INVENTION

The present invention relates generally to medical systems that utilize piezoelectric-vibration, and particularly to phacoemulsification systems.

BACKGROUND OF THE INVENTION

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques to control ultrasonic-vibration-based therapy were proposed in the patent literature. For example, U.S. Pat. No. 7,135,029 describes an ultrasonic surgical system comprising a generator and an instrument comprising: a housing; a transducer; a semi-permeable membrane; a pharmaceutical agent; and an agent delivery system. The transducer is adapted to convert the electrical energy of the generator into mechanical energy. The pharmaceutical agent, delivered into a chamber of the semi-permeable membrane, is driven through the semi-permeable membrane by the mechanical energy. The present invention contemplates one or a plurality of feedback devices used within a system feedback loop to control, for example, the therapy source, pulsing, treatment time, and/or rate of drug infusion, in order to optimize the ablative and drug activation-based treatments. In an embodiment, the feedback device is selected from the group consisting of a non-thermal response monitor, a thermal response monitor, a cavitation monitor, a streaming monitor, an ultrasonic imaging device, a drug activation monitor, an infusion rate control, a source control, a duty cycle control, a piezo sensor, a piezo receiver, a thermocouple, and a frequency control.

As another example, U.S. Pat. No. 6,193,683 describes phacoemulsification apparatus that includes a handpiece having a needle and electrical apparatus for ultrasonically vibrating the needle. A power source provides electrical power to the handpiece electrical apparatus and irrigation fluid is provided to the handpiece needle and aspirated therefrom during phacoemulsification. Temperature sensors are provided for determining the temperature of the handpiece needle and a control unit is provided for varying a power level provided the handpiece electrical apparatus and the power source in response to the needle temperature. Alternatively, the control unit functions to vary either irrigation fluid flow or aspiration fluid flow from the handpiece in response to the needle temperature.

Chinese Patent, CN 1,299,657 describes a phacoemulsification instrument comprising a needle treatment section and a cooling section. Thermocouples transmit temperature signals to a control circuit through a temperature measurement circuit to prevent thermal damage to the intraocular tissue. In one embodiment, a needle treatment section is welded with one thermocouple, and the refrigerant throttled section capillary has a second thermocouple fitted with, so as to control use of a refrigerant fluid to prevent the thermal damage.

SUMMARY OF THE INVENTION

An embodiment of the present invention that is described hereinafter provides a phacoemulsification device including a needle, one or more piezoelectric crystals, and one or more thermocouples. The needle is configured for insertion into a lens capsule of an eye. The one or more piezoelectric crystals are configured to vibrate the needle. The one or more thermocouples are thermally coupled directly to the respective piezoelectric crystals and are configured to measure respective temperatures of the one or more piezoelectric crystals as the crystals vibrate, and to output indications of the respectively measured temperatures.

In some embodiments, the one or more piezoelectric crystals include two or more piezoelectric crystals that are configured to vibrate in respective different resonant modes, and the one or more thermocouples include two or more thermocouples thermally coupled directly to the two or more respective piezoelectric crystals.

There is additionally provided, in accordance with another embodiment of the present invention, a phacoemulsification apparatus including a phacoemulsification device and a processor. The phacoemulsification device includes a needle configured for insertion into a lens capsule of an eye, one or more piezoelectric crystals that are configured to vibrate the needle, and one or more thermocouples that are thermally coupled directly to the respective piezoelectric crystals and are configured to measure respective temperatures of the piezoelectric crystals as the crystals vibrate, and to output indications of the respectively measured temperatures. The processor is configured to adaptively adjust one or more frequencies of one or more drive signals that drive the one or more piezoelectric crystals, based on the outputted temperature indications.

In some embodiments, the one or more piezoelectric crystals are configured to vibrate in one or more respective resonant modes having one or more respective resonant frequencies, and the processor is configured to adaptively adjust the one or more frequencies of the one or more drive signals to compensate for temperature-induced variations in the one or more resonant frequencies of the one or more piezoelectric crystals.

There is further provided, in accordance with another embodiment of the present invention, a driving method for one or more piezoelectric crystals having respective resonant modes, the method including generating one or more drive signals having respective frequencies. The one or more piezoelectric crystals is driven with the respective one or more drive signals. One or more respective temperatures of the one or more piezoelectric crystals are measured as the one or more piezoelectric crystals vibrate. The one or more frequencies of the one or more drive signals is adaptively adjusted based on the one or more measured temperatures.

The present invention will be more fully understood from the following detailed description of the embodiments thereof, taken together with the drawings in which:

DETAILED DESCRIPTION OF EMBODIMENTS

Overview

Figure 1:
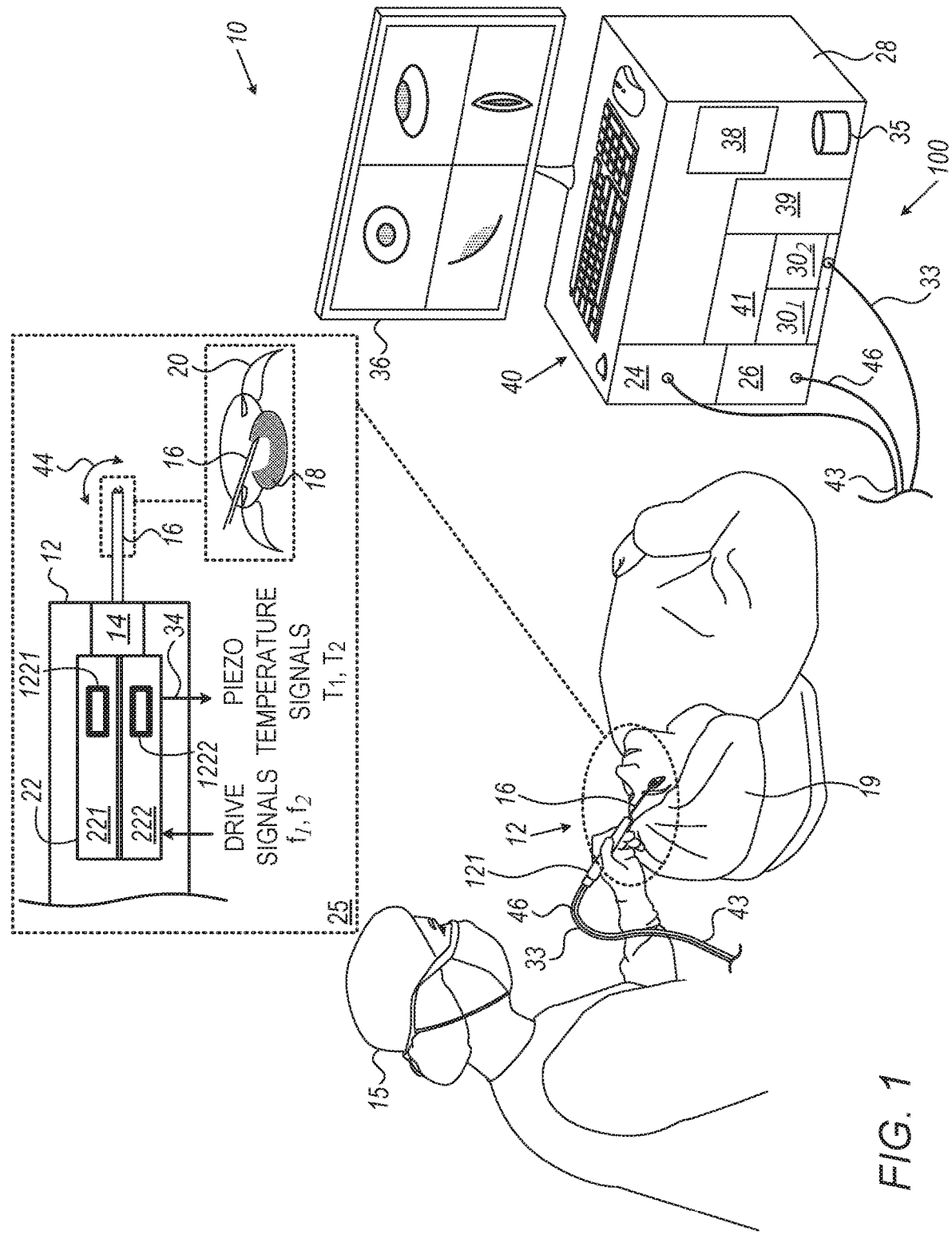
FIG. 1 is a pictorial view, along with a block diagram, of a phacoemulsification apparatus comprising a phacoemulsification probe comprising two thermocouples, disposed on two respective piezoelectric vibrating crystals, in accordance with an embodiment of the present invention.

A phacoemulsification system typically drives a piezoelectric actuator included in a phacoemulsification probe/handpiece to vibrate a needle of the phacoemulsification probe during a cataract procedure. The piezoelectric actuator of the phacoemulsification probe may be designed to vibrate, in resonance, in one or more modes, where each mode has a given "natural" resonant frequency. For example, a multi-resonance mode might yield a complex vibration profile that combines longitudinal, transverse, and torsion vibrations, each with its own resonant frequency. Such a mode may have a complex customizable vibration profile that may allow a physician to better perform phacoemulsification.

However, the ocular media in which the needle vibrates induces changes in the mechanical load on the needle, and this causes the vibration frequencies to drift away from resonance, for example, as the crystal (or crystals) heat up when loaded by ocular media. The changing (e.g., drifting) frequencies result in reduced amplitude of vibration (and therefore in inefficient vibration).

Moreover, if the resonant frequencies of the piezoelectric actuator change with crystal temperature, and the piezoelectric actuator is still powered with signals having the same frequencies (i.e., with part or all of the frequencies being off-resonance), the piezoelectric actuator may heat further. The additional heat may lead to further changes in the resonant frequencies, which in turn may lead to further heat, and so on.

Inadequate control of the vibration frequencies can also lead to a hazard as the phacoemulsification needle becomes too hot for the eye. For example, the phacoemulsification needle could reach a temperature of 42° C., above which the proteins in the eye may coagulate, which is very dangerous for the eye. While irrigation may be used to reduce the temperature of the phacoemulsification needle, irrigation presents its own problems. For example, irrigation without carefully matched aspiration can increase internal eye pressure to dangerous levels, whereas too much aspiration can lead to eye collapse. Moreover, irrigation may not be sufficient to adequately cool the phacoemulsification needle.

Embodiments of the present invention that are described hereinafter provide methods and apparatus that measure a piezoelectric crystal temperature by a thermocouple disposed on the crystal, and use the measured temperature as a feedback signal in a control loop of the piezo-driving system. The control loop adapts driving frequencies so as to maintain the crystal to vibrate in resonance. The thermocouple is thermally coupled directly to the crystal (e.g., directly disposed, or attached to the crystal) so as to provide (a) accurate temperature measurement of the crystal itself, and (b) a fast-response temperature feedback signal, to a vibration control circuitry, or a processor, to adjust the driving signal frequency responsively to the real-time temperature reading from the crystal, so as to keep the crystal vibrating at resonance.

The term "thermally coupled directly to the crystal," as used in the embodiments of the current invention, aim to cover multiple ways a thermocouple can be thermally coupled to a crystal, such as, but not limited to, the thermocouple being attached to a good heat conductor element that is itself in good thermal contact with the crystal. For example, the thermocouple may be attached to a thin metal plate that is itself attached to the crystal, or the thermocouple may be attached to the crystal using a heat-conductive glue. All such and other variations should be understood as covered by the disclosed description. Regardless of the coupling method between the thermocouple and the crystal, the thermocouple aims to measure the actual temperature of the crystal, not the ambient temperature or other temperature.

In an embodiment, the one or more piezoelectric crystals are configured to vibrate in one or more respective resonant modes having one or more respective resonant frequencies, and the processor is configured to adaptively adjust the one or more frequencies by compensating for temperature-induced variations in the one or more resonant frequencies of the one or more piezoelectric crystals.

As noted above, phacoemulsification typically may use two or more modes of needle vibration in order to carve up the cataract lens of the eye. Some embodiments of the present invention that are described hereinafter use two or more temperature-controlled piezoelectric crystals that drive each of the crystals independently in a selected resonant mode, typically at different frequencies. To achieve the aforementioned piezo-temperature feedback signals, two or more respective thermocouples are each disposed on a crystal. Some embodiments provide individual processor-controlled drive modules, described below, to drive each resonant-frequency mode of vibration of the two or more piezoelectric crystals, using real-time thermocouple data.

Disposing the thermocouple to a crystal results in a fast temperature reading, and therefore fast response time to a changing temperature reading, which is required to maintain the vibration frequency resonance. Since each crystal is required to vibrate only in one mode, there is less interaction between the modes, and thus it is much easier to generate the required vibrations with the real-time temperature feedback signal from each crystal.

System Description

FIG. 1 is a pictorial view, along with a block diagram, of a phacoemulsification apparatus 10 comprising a phacoemulsification probe 12 comprising two thermocouples 1221 and 1222, disposed on two respective piezoelectric vibrating crystals 221 and 222, in accordance with an embodiment of the present invention. As seen in the pictorial view of phacoemulsification apparatus 10, and the block diagram in inset 25, phacoemulsification probe 12 comprises a needle 16 configured for insertion into a lens capsule 18 of an eye 20 of a patient 19 by a physician 15. Needle 16 is coupled with a horn 14 comprised in probe 12, and is shown in inset 25 as a straight needle. However, any suitable needle may be used with the phacoemulsification probe 12, for example, a curved or bent tip needle commercially available from Johnson & Johnson Surgical Vision, Inc., Santa Ana, Calif., USA.

A piezoelectric actuator 22 inside probe 12 is configured to use piezoelectric crystals 221 and 222 to vibrate horn 14 and needle 16 in one or more resonant vibration modes of the combined horn and needle element. The vibration of needle 16 is used to break a cataract into small pieces during the phacoemulsification procedure.

In the shown embodiment, console 28 comprises a dual-channel piezoelectric drive system 100 comprising drive modules $30_1$ and $30_2$, each coupled, using electrical wiring running in cable 33, with each of the two piezoelectric crystals 221 and 222 of actuator 22. Drive-modules $30_1$ and $30_2$ are controlled by a processor 38 and convey processor-controlled driving signals via cable 33 to adjust frequencies of a multi-resonance mode of piezoelectric actuator 22 to maintain needle 16 at maximal vibration along a trajectory 44. Each of the drive modules may be realized in hardware or software, for example, in a proportional-integral-derivative (PID) control architecture.

Drive system 100 excites, using drive-modules $30_1$ and $30_2$, each one of the crystals independently in a selected resonant mode, typically at different frequencies $f_1$ and $f_2$. For example, crystal 221 is vibrated in a longitudinal direction, whereas crystal 222 is vibrated in an axial direction. Since each of crystals 221 and 222 are required to vibrate only in one mode, there is less interaction between the modes, and thus it is much easier to generate and control the required vibrations.

Piezo temperatures $T_1$ and $T_2$ signals 34, sensed by thermocouples 1221 and 1222, are conveyed over cable 33 to a temperature sensing module 39. By directly attaching the crystals to the thermocouples, module 39 can provide fast real-time feedback temperature data (e.g., control signals based on sensed temperatures $T_1$ and $T_2$) to processor 38, which uses the real-time data to estimate the vibration frequencies of needle 16, and correspondingly to command piezoelectric drive modules how to maintain the vibration of needle 16 at resonance.

For example, processor 38 may calculate derivatives of the sensed $T_1$ and $T_2$ signals and, using those derivatives, adjust the resonant frequencies so as to reverse a sign of the derivatives (e.g., a positive derivative indicates an increased temperature, that in turn indicates drift from resonance frequency, and henceforth causes the processor to induce a corrective adjustment to bring a frequency back to resonance, as confirmed by lowered temperature signals). In general, however, numerous other control schemes may utilize the sensed signals $T_1$ and $T_2$ in different ways to follow the varying resonant frequencies.

Processor 38 is further configured to use a switching circuitry 41 to connect drive modules $30_1$ and/or $30_2$ to vibrate needle 16 in one of several prespecified trajectories.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

Processor 38 may receive user-based commands via a user interface 40, which may include setting a vibration mode and/or frequency of the piezoelectric actuator 22, adjusting the vibration mode and/or frequency of the piezoelectric actuator 22, setting or adjusting a stroke amplitude of the needle 16, setting or adjusting an irrigation and/or aspiration rate of the pumping sub-system 26. Additionally, or alternatively, processor 38 may receive user-based commands from controls located in handle 121, to, for example, select trajectory 44, or another trajectory, for needle 16. In an embodiment, user interface 40 and display 36 may be one and the same such as a touch screen graphical user interface.

In the shown embodiment, during the phacoemulsification procedure, a pumping sub-system 24 comprised in a console 28 pumps irrigation fluid from an irrigation reservoir to needle 16 to irrigate the eye. The fluid is pumped via a tubing line 43 running from the console 28 to the probe 12. Waste matter (e.g., emulsified parts of the cataract) and eye fluid are aspirated via needle 16 to the collection receptacle by a pumping sub-system 26 also comprised in console 28 and using another tubing line 46 running from probe 12 to console 28. As seen in FIG. 1, processor 38 may present results of the procedure on a display 36.

The apparatus shown in FIG. 1 may include further elements, which are omitted for clarity of presentation. For example, physician 15 typically performs the procedure using a stereo-microscope or magnifying glasses, neither of which are shown. Physician 15 may use other surgical tools in addition to probe 12, which are also not shown in order to maintain clarity and simplicity of presentation.

While FIG. 1 shows a piezoelectric actuator 22 comprising two piezoelectric crystals, in general, piezoelectric actuator 22 may comprise one or more piezoelectric crystals. For example, piezoelectric actuator 22 may comprise three piezoelectric crystals, each of which vibrates needle 16 independently at a spatially different direction (e.g. longitudinal, axial, and torsional). Each of the crystals may be disposed with a thermocouple to generate a temperature control signal for maintaining the crystal vibrating at resonance, as described above.

Method of Controlling Phacoemulsification Needle Vibration Frequencies

Figure 2:
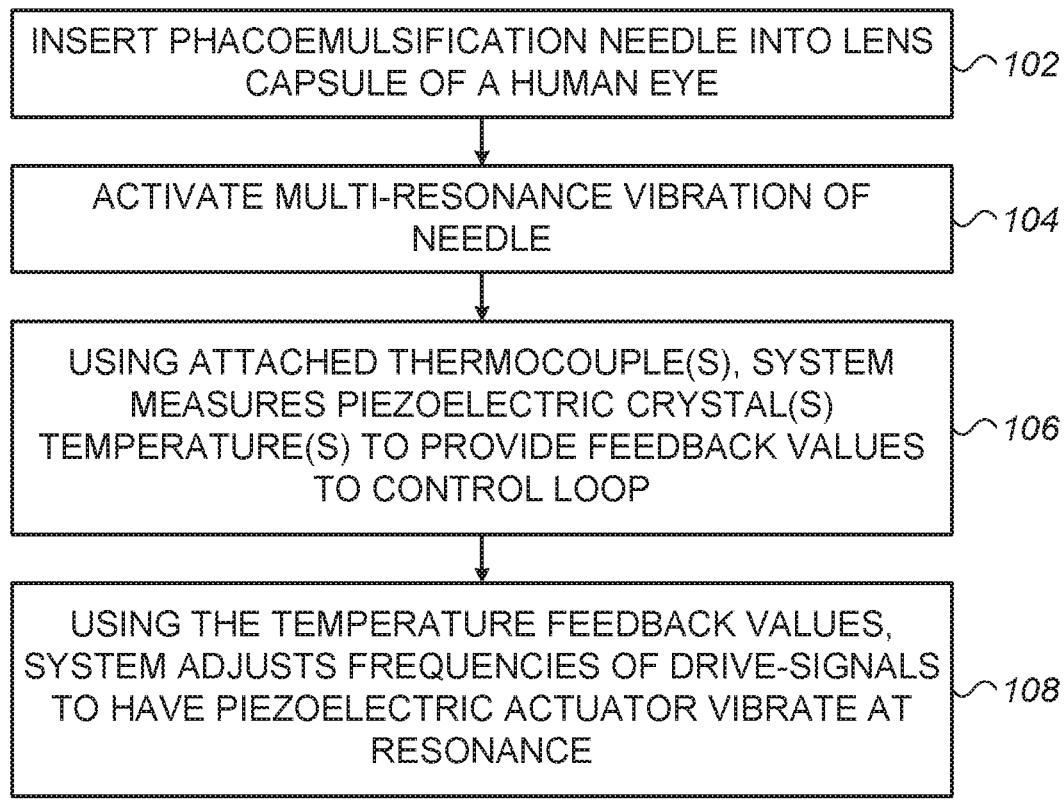
FIG. 2 is a flow chart schematically illustrating a method for controlling the phacoemulsification probe of FIG. 1 using temperature signals from the piezo-disposed thermocouples, in accordance with an embodiment of the present invention.

FIG. 2 is a flow chart schematically illustrating a method for controlling phacoemulsification probe 12 of FIG. 1 using temperature signals from the piezo-disposed thermocouples 1221 and 1222, in accordance with an embodiment of the present invention. The algorithm, according to the presented embodiment, carries out a process that begins with physician 15 inserting phacoemulsification needle 16 of probe 12 into a lens capsule 18 of an eye 20, at a probe insertion step 102.

Next, physician 15 activates, for example using a control over handle 121 or a foot pedal (not shown), probe 12 to vibrate needle 16 in complex trajectory 44, comprising, for example, a combination of longitudinal, transverse, and/or torsional, at a needle vibrating step 104.

Using signals acquired by thermocouples 1221 and 1222, processor 38 calculates changes in piezo-drive frequencies $f_1$ and $f_2$, at a feedback step 106.

Finally, using the feedback loop that receives the temperature feedback signals, processor 38 commands drive system 100 to use drive-modules $30_1$ and $30_2$ to excite crystals 221 and 222 at the adjusted drive frequencies $f_1$ and $f_2$ such that piezoelectric actuator 22 continues to vibrate at resonance, at a vibration controlling step 108.

The example flow chart shown in FIG. 2 is chosen purely for the sake of conceptual clarity. For example, additional steps such as cutting, irrigating, and inspecting the eye are omitted for simplicity and clarity of presentation.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification device, comprising:
a needle configured to vibrate;
one or more piezoelectric crystals that are configured to vibrate the needle; and
one or more thermocouples that are thermally coupled directly to the respective piezoelectric crystals and are configured to measure respective temperatures of the one or more piezoelectric crystals as the crystals vibrate, and to output indications of the respectively measured temperatures.

2. The phacoemulsification device according to claim 1, wherein the one or more piezoelectric crystals comprise two or more piezoelectric crystals that are configured to vibrate in respective different resonant modes, and wherein the one or more thermocouples comprise two or more thermocouples thermally coupled directly to the two or more respective piezoelectric crystals.

3. A phacoemulsification apparatus, comprising:
a phacoemulsification device comprising:
a needle configured to vibrate;
one or more piezoelectric crystals that are configured to vibrate the needle; and
one or more thermocouples that are thermally coupled directly to the respective piezoelectric crystals and are configured to measure respective temperatures of the piezoelectric crystals as the crystals vibrate, and to output indications of the respectively measured temperatures; and
a processor, which is configured to adaptively adjust one or more frequencies of one or more drive signals that drive the one or more piezoelectric crystals, based on the outputted temperature indications.

4. The phacoemulsification apparatus according to claim 3, wherein the one or more piezoelectric crystals are configured to vibrate in one or more respective resonant modes having one or more respective resonant frequencies, and wherein the processor is configured to adaptively adjust the one or more frequencies of the one or more drive signals to compensate for temperature-induced variations in the one or more resonant frequencies of the one or more piezoelectric crystals.

5. A driving method for one or more piezoelectric crystals having respective resonant modes, the method comprising:
generating one or more drive signals having respective frequencies;
driving the one or more piezoelectric crystals with the respective one or more drive signals;
measuring one or more respective temperatures of the one or more piezoelectric crystals as the one or more piezoelectric crystals vibrate; and
adaptively adjusting the one or more frequencies of the one or more drive signals based on the one or more measured temperatures.

6. The driving method according to claim 5, wherein the one or more piezoelectric crystals are configured to vibrate in one or more respective resonant modes having one or more respective resonant frequencies, and wherein adaptively adjusting the one or more frequencies comprises compensating for temperature-induced variations in the one or more resonant frequencies of the one or more piezoelectric crystals.

* * * * *